United States Patent
Toyoda

(10) Patent No.: US 6,264,643 B1
(45) Date of Patent: Jul. 24, 2001

(54) PULL-ON TYPE DISPOSABLE DIAPER

(75) Inventor: Harumitsu Toyoda, Tochigi-ken (JP)

(73) Assignee: Kao Corporation, Tokyo (JP)

( * ) Notice: Subject to any disclaimer, the term of this patent is extended or adjusted under 35 U.S.C. 154(b) by 956 days.

(21) Appl. No.: 08/550,521

(22) Filed: Oct. 30, 1995

Related U.S. Application Data

(63) Continuation of application No. 08/293,097, filed on Aug. 19, 1994, now abandoned.

(30) Foreign Application Priority Data

| | | |
|---|---|---|
| Sep. 2, 1993 | (JP) | 5-218912 |
| Oct. 26, 1993 | (JP) | 5-267064 |

(51) Int. Cl.$^7$ .................................................. A61F 13/15
(52) U.S. Cl. ........................... 604/385.29; 604/385.3; 604/396; 604/385.13
(58) Field of Search ................... 604/385.1–387, 604/389–396, 385.01

(56) References Cited

U.S. PATENT DOCUMENTS

| | | | | |
|---|---|---|---|---|
| 4,205,679 | * | 6/1980 | Repke et al. | 604/385.2 |
| 4,319,572 | * | 3/1982 | Widlund et al. | 604/385.2 |
| 4,641,381 | | 2/1987 | Heran et al. | |
| 4,938,757 | | 7/1990 | Van Gompel et al. | |
| 4,940,464 | * | 7/1990 | Van Gompel et al. | 604/385.2 |
| 4,963,140 | * | 10/1990 | Robertson et al. | 604/391 |
| 5,151,092 | * | 9/1992 | Buell et al. | 601/385.2 |
| 5,591,155 | * | 1/1997 | Nichikawa et al. | 604/385.2 |

FOREIGN PATENT DOCUMENTS

| | | |
|---|---|---|
| 0 320991 | 6/1989 | (EP) . |
| 0 487921 | 3/1992 | (EP) . |
| 0526868 | 2/1993 | (EP) . |
| 0547497 | 6/1993 | (EP) . |
| 2 253131 | 9/1992 | (GB) . |
| 24364 | 1/1990 | (JP) . |
| 21401631 | 5/1990 | (JP) . |
| 3176051 | * 7/1991 | (JP) ...................................... 604/394 |
| 3176052 | * 7/1991 | (JP) ...................................... 604/394 |
| 4289201 | 10/1992 | (JP) . |
| 4364845 | 12/1992 | (JP) . |
| 4354948 | * 12/1992 | (JP) ...................................... 604/394 |
| 4371147 | * 12/1992 | (JP) .................................. 604/385.2 |
| 4371148 | * 12/1992 | (JP) .................................. 604/385.2 |
| 5192366 | * 8/1993 | (JP) ...................................... 604/396 |
| 9 309746 | 5/1993 | (WO) . |
| 9 317648 | 9/1993 | (WO) . |

* cited by examiner

Primary Examiner—John G. Weiss
Assistant Examiner—K. M. Reichle
(74) Attorney, Agent, or Firm—Birch, Stewart, Kolasch & Birch, LLP

(57) ABSTRACT

A shorts type disposable diaper includes a body having a liquid permeable topsheet, a liquid impermeable backsheet, and an absorbent member interposed between the topsheet and the backsheet. The body includes a stomach-side portion which is located on the stomach side of a diaper wearer when the diaper is worn, a back-side portion which is located on the back side of the wearer when the diaper is worn, and a crotch portion which is located between the stomach-side portion and the back-side portion. The body has a pair of first expansible side panels, each of the first expansible side panels being affixed to each longitudinal side of the stomach-side portion and a pair of second expansible side panels, each of the second expansible side panels being affixed to each longitudinal side of the back-side portion. The first expansible side panels of the stomach-side portion are affixed to the second expansible side panels of said back-side portion to thereby define a waist opening portion, a pair of leg opening portions and a body-surrounding portion located around the wearer's body when the diaper is worn. Elastic members are arranged on an area adjacent to the waist opening portion and on the body-surrounding portion in the stomach-side and back-side portions. A substantially continuous gather is formed along an entire periphery of the diaper through the stomach-side portion, the back-side portion and the first and second expansible panels.

8 Claims, 3 Drawing Sheets

PULL-ON TYPE DISPOSABLE DIAPER

This application is a continuation of application Ser. No. 08/293,097 filed on Aug. 19, 1994, now abandoned.

BACKGROUND OF THE INVENTION

1. Field of the Invention

This invention relates to a disposable diaper for use of infants, incontinent persons, and adults.

2. Description of the Related Art

In general, a disposable diaper is of a flat type and usually comprises an elongated body including a liquid permeable topsheet, a liquid impermeable backsheet, and an absorbent member interposed between the topsheet and the backsheet. The elongated body has a stomach-side portion which is located on the stomach side of a diaper wearer when the diaper is worn, and a back-side portion which is located on the back side of the wearer when the diaper is worn.

Recently, there has been proposed a pull-on type disposable diaper in which a pair of leg opening portions and a single waist opening portion are formed by affixing the stomach-side portion to the back-side portion through a pair of side flaps which are formed on the body along its longitudinal sides (see Japanese Laid-Open Patent Application No. Sho 61-207605).

In the pull-on type disposable diaper above outlined, the pair of leg opening portions are expansible so that the diaper fits well to the body contour of the diaper wearer. Usually, the wearer puts on the diaper while standing. Therefore, this diaper is used as a toilet training device for encouraging the infant wearer to finish with a diaper (i.e., to be well without the diaper), or for the use of incontinent persons or adults who can walk.

Also, the above-mentioned pull-on type disposable diaper has, when compared with a so-called flat-type diaper, the features in the respect that the diaper wearer can pull it upwardly or downwardly by himself/herself just like a normal undergarment. However, in order for the diaper wearer to easily put on the diaper by himself/herself and not to allow the discharged materials to leak, an excellent fit is required for the pull-on type disposable diaper. Furthermore, compliance enough to follow the busy movements of the diaper wearer is required.

In order to fulfill these requirements, Japanese Laid-Open Patent Application No. Hei 2-4364 proposes a pull-on type disposable diaper in which side portions for affixing a stomach-side portion of a body to a back-side portion thereof are each provided with a side panel (side portion), and edge areas of the stomach and back-side portions of the body are provided with elastic members, respectively.

However, in the pull-on type disposable diaper proposed in the above-mentioned Laid-Open Patent Application No. Hei 2-4364, since the side panel is of a single member and each member has the same degree of expansive property, a tightening force must be increased in order to prevent the diaper from slipping down and in order to enhance the fit. This gives an undue sense of oppression to the diaper wearer and spoils the easiness at the time the diaper is put on and taken off. This further causes the sense of oppression to be concentrated on both sides of the wearer's waist portion to make the wearer's skin irritated.

Furthermore, since the stress mostly concentrates on the area around each leg of the diaper wearer by the side panel when the diaper is worn, the area around the wearer's waist portion is comparatively loosened and therefore, the diaper is liable to slip down as the wearer moves actively and due to the weight of the discharged materials. Since the crotch portion also becomes loosened, the discharged materials are liable to leak. In order to avoid the foregoing, another type of disposable diaper has been proposed having a gather in the crotch portion thereby preventing leakage. However, this disposable diaper actually has the shortcoming in that when the waist portion becomes comparatively loosened in accordance with busy movements of the infant diaper wearer, the diaper slips down to form a space between the diaper and its wearer and the body fluid tends to leak through this space.

Furthermore, the above-mentioned pull-on type disposable diaper having side panels has the shortcoming in that a baby wearer finds it comparatively difficult to put on. Also, in the conventional pull-on type disposable diaper, since the expansible member of the waist portion is provided only to the waist opening portion, a gather, which is formed by the expansible member, is not continuously connected to side panel and therefore, a space is occasionally formed between the waist portion of the diaper and its wearer. Accordingly, it has the shortcoming in that the expansible member fails to expand or contract sufficiently, and the diaper fails to fit well to the wearer around his/her body, thereby allowing the discharged materials to leak through the space formed between the diaper and its wearer, and allow the diaper to slip down as a result of a decrease in a degree of compliance to the busy movements of the wearer.

SUMMARY OF THE INVENTION

It is therefore an object of the present invention to provide a pull-on type disposable diaper which is excellent in fit at a body-surrounding portion, in ability for preventing the diaper from slipping down and in ability for preventing discharged materials from leaking.

The present invention has achieved the above object by providing a pull-on type disposable diaper comprising a body having a liquid permeable topsheet, a liquid impermeable backsheet, and an absorbent member interposed between said topsheet and said backsheet, characterized in that;

said body comprises a stomach-side portion which is located on the stomach side of a diaper wearer when the diaper is worn, a back-side portion which is located on the back side of the wearer when the diaper is worn, and a crotch portion which is located between said stomach-side portion and said back-side portion;

said body has a pair of first expansible side panels, each of said first expansible side panels being affixed to each longitudinal side of said stomach-side portion and a pair of second expansible side panels, each of said second expansible side panels being affixed to each longitudinal side of said back-side portion;

said first expansible side panels of said stomach-side portion are affixed to said second expansible side panels of said back-side portion to thereby define a waist opening portion, a pair of leg opening portions and a body-surrounding portion located around the wearer's body when the diaper is worn;

elastic members are arranged on an area adjacent to said waist opening portion and on said body-surrounding portion in said stomach-side and back-side portions; and a substantially continuous gather is formed along an entire periphery of the diaper through said stomach-side portion, said back-side portion and said first and second expansible panels.

Since the pull-on type disposable diaper of the present invention has the expansible side panels and the elastic members provided in the areas adjacent to the waist opening portion and the body-surrounding portion, a substantially continuous gather is formed along the entire periphery of the body-surrounding portion when the diaper is worn.

Accordingly, this disposable diaper can well fit to each part of the wearer's body depending on the wearer's body contour and no undue sense of oppression is given to the wearer. Eventually, any leak of the discharged materials and slip-down of the disposable diaper can be prevented.

The pull-on type disposable diaper of the present invention is excellent in fit property of the body-surround area, in ability for preventing the diaper from slipping down and in ability for preventing discharged materials from leaking. Furthermore, this type of disposable diaper can easily be applied to or removed from a wearer such as an infant, in his/her standing or sitting state. In addition, this diaper can be adjusted in size depending on the physical constitution of the wearer, and in the case where a tape for discard is provided, it becomes easy to discard the diaper after the waste materials are discharged.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Several embodiments of the present invention will now be described in detail with reference to the accompanying drawings.

Figure 1:
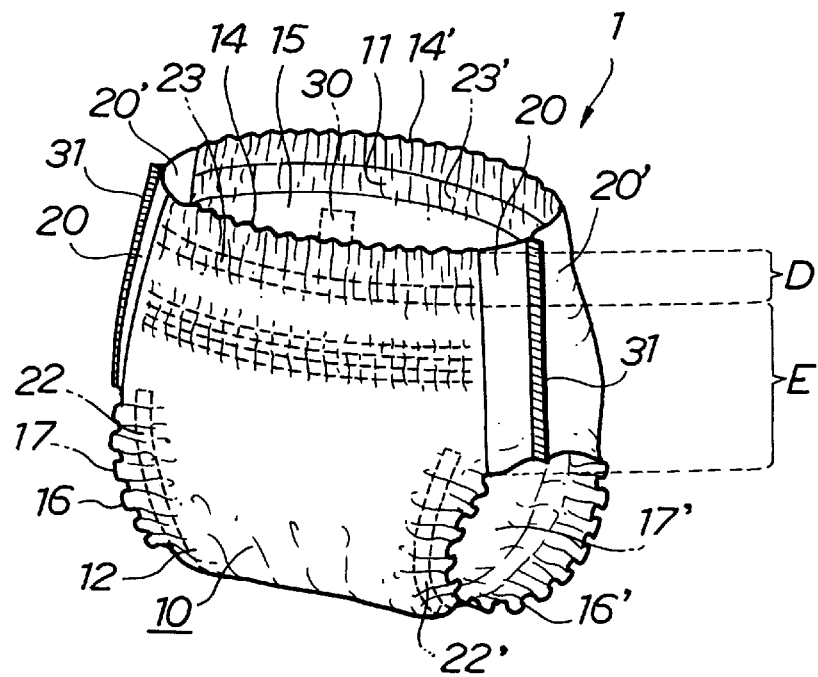
FIG. 1 is a perspective view showing one embodiment of a pull-on type disposable diaper of the present invention.
Figure 2:
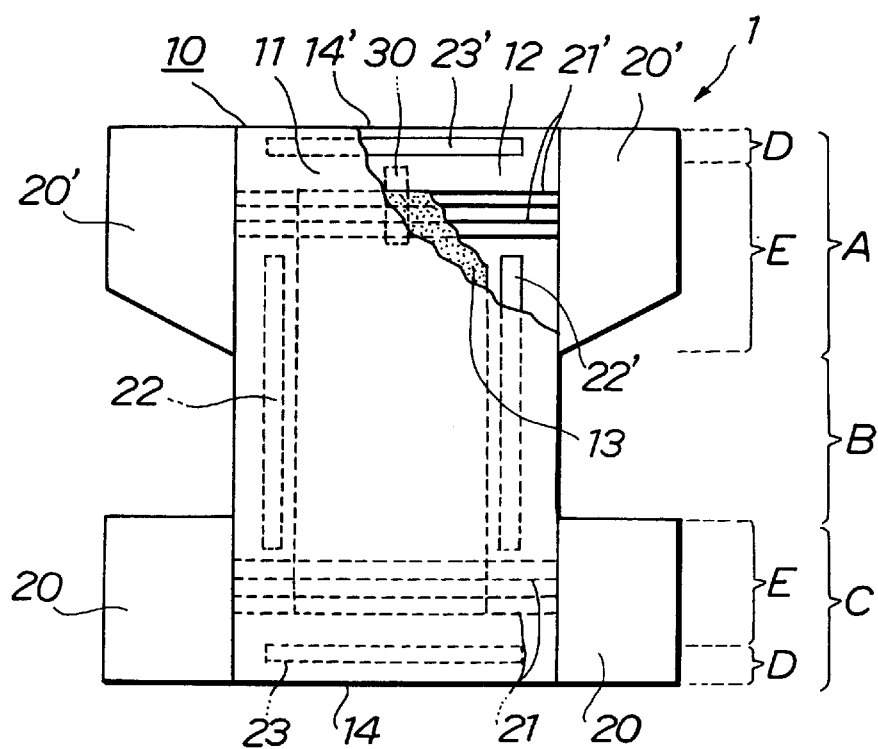
FIG. 2 is a partially cut-away view of the disposable diaper of FIG. 1.

FIG. 1 is a perspective view showing one embodiment of a pull-on type disposable diaper of the present invention, and FIG. 2 is a partially cut-away view of the disposable diaper shown in FIG. 1.

As shown in FIGS. 1 and 2, the disposable diaper 1 of this embodiment comprises a rectangular body 10 having opposing longitudinal sides and a liquid permeable topsheet 11, a liquid impermeable backsheet 12, and an absorbent member 13 interposed between the topsheet 11 and the backsheet 12. The body 10 has a stomach-side portion C which is located on the stomach side of a diaper wearer when the diaper is worn, a back-side portion A which is located on the back side of the wearer when the diaper is worn, and a crotch portion B which is located between the stomach-side portion C and the back-side portion A. A fringe of each vertical side, this side constituting a part of a longitudinal side of the diaper body 10, of the stomach-side portion C and a fringe of each vertical side, this side also constituting a part of a longitudinal side of the diaper body 10, of the back-side portion A are provided with a pair of separately formed first expansible side panels 20 and a pair of separately formed second expansible side panels 20' respectively, which are affixed thereto. The first expansible side panels 20 of the stomach-side portion C are affixed to the second expansible side panels 20' of the back-side portion A, respectively, thereby forming a waist opening portion 15 and a pair of leg opening portions 17 and 17'. Waist portion elastic members 23 and 23' and waist-surrounding portion elastic members 21 and 21' are arranged on each area D adjacent to the waist opening portion 15 and on each body-surrounding portion E which is located around the wearer's body when the diaper 1 is worn, in the stomach and back-side portions C and A. Waist portion elastic members 23 and 23' have opposing ends which terminate within the body, as shown in FIG. 2. A substantially continuous gather is formed along an entire periphery of the diaper 1 through the stomach-side portion C, the back-side portion A and the first and second expansible side panels 20 and 20'.

More specifically, the absorbent member 13 is of a rectangular configuration and fixedly sandwiched between the topsheet 11 and the backsheet 12. Strip-like leg portion elastic members 22 and 22' are respectively laid on opposite longitudinal sides (leg portions 16, 16') of the absorbent member 13 between the topsheet 11 and the backsheet 12. As shown in FIG. 1, the elastic members 22 and 22' are contracted, in their natural or free states, to form leg gathers, respectively, so that the diaper may fit well to the crotch portion.

Next, acceptable materials for forming various component members of the disposable diaper according to this embodiment will be described.

With respect to an acceptable first material for forming the topsheet 11, a liquid permeable sheet capable of permeating the discharged materials to the absorbent member 13 and having the feel similar to an undergarment is preferred. Examples of the preferred liquid permeable sheet can include woven fabrics, nonwoven fabrics, perforated films, and the like.

The backsheet 12 can be preferably of a liquid impermeable vapor permeable second material different from the first material, including a sheet which is made by adding a filler to a thermoplastic resin and stretched, or of a textile fabric.

The absorbent member 13 can be preferably composed chiefly of a comminuted pulp or fibrillated pulp combined with a water absorbent polymer. The absorbent member 13 can also be preferably prepared by mixing with a thermoplastic resin, a cellulosic fiber, a water absorbent polymer or the like and subjecting the mixture to heat treatment. The water absorbent polymer may exist in any of the upper layer, intermediate layer and lower layer of the absorbent member 13, or may also be mixed with pulp. The water absorbent polymer is preferably of granules having a water absorption ability capable of absorbing and holding a liquid more than twenty times its dead weight and is preferably gelled when it absorbs water. Such water absorbent polymer preferably may include a saponified graft copolymer of starch and acrylic acid or salts thereof, a crosslinked polymer of sodium carboxymethyl-cellulose, a polymer of acrylic acid or salts thereof, or the like.

The leg portion elastic members 22 and 22' may be formed, without any particular limitation, of an elastic member which is composed of, for example, a natural rubber, a synthetic rubber, a foamed polyurethane or the like. Although the strip-like elastic members are used in this embodiment, a single or a plurality of string-like elastic members may be employed.

A discarding tape 30 is provided on the surface of the backsheet 12 at a generally central portion of the back-side portion A. The discarding tape 30 is preferably composed of a conventional tape material with an adhesive applied thereto. The adhesive may be a conventional one which is composed of a hot melt resin or emulsions such as, for example, a styrene-butadiene block copolymer, a styrene-isoprene block copolymer, an acrylic polyester, an acrylic copolymer, poly(vinyl acetate), and an ethylene-vinyl acetate copolymer. Also, the discarding tape 30 may be affixed to a tape affixing area by means of a physical structure such as a magic tape.

Owing to a provision of the discarding tape 30, the disposable diaper 1 can be discarded by rolling up the diaper body in a compact size and fastening the same with the discarding tape 30 after the waste materials are discharged. Since the discharged waste materials can be confined within the diaper body, the disposable diaper can be handled or processed in a sanitary manner and discarded with ease.

The features of the disposable diaper of this embodiment will now be described. As shown in FIG. 2, the body 10 has a stomach-side portion C which is located on the stomach side of the diaper wearer when the diaper is worn, a back-side portion A which is located on the back side of the wearer when the diaper is worn, and crotch portion B. A fringe of each vertical side of the stomach-side portion C and a fringe of each vertical side of the back-side portion A are provided with first expansible side panels 20 and second expansible side panels 20' respectively, which are affixed to thereto.

The first and second expansible side panels 20 and 20' are affixed to the fringes of the vertical sides of the stomach-side portion C and the back-side portion A, respectively, by affixing means including heat sealing, ultrasonic sealing, adhesive sealing or any other suitable affixing means.

As shown in FIG. 1, the first expansible side panels 20, 20 of the stomach-side portion C are affixed to the second expansible side panels 20', 20' of the back-side portion A in such a manner that the topsheet 11 side of the vertical side portions of the first expansible side panels 20 contact the topsheet 11 side of the vertical side portions of the second expansible side panels 20'. By this, the waist opening portion 15 and the pair of leg opening portions 17 and 17' are defined. Reference numeral 31 denotes a strip-like seal area which is formed by the above-mentioned affixing.

The above-mentioned affixing can be made by heat sealing, ultrasonic sealing, adhesive sealing or any other suitable means.

In the areas D adjacent to the waist opening portion of the stomach-side portion C and the back-side portion A, the strip-like waist portion elastic members 23 and 23' are arranged substantially in parallel with a peripheral edge of the waist opening portion, i.e., the front and back waist portions 14 and 14'. Likewise, in the body-surrounding portion E of the stomach-side portion C and the back-side portion A, the string-like body-surrounding portion elastic members 21 and 21' are arranged four each in such a manner as to be in parallel with the front and back waist portions 14 and 14' and sandwiched between the backsheet 12 and the absorbent member 13. Owing to the arrangement of the body-surrounding portion elastic members 21 and 21' and the waist portion elastic members 23 and 23', the substantially continuous gather is formed along an entire periphery of the diaper 1 through the stomach-side portion C, the back-side portion A and the first and second expansible side panels 20 and 20', i.e., outer peripheral surfaces (the surface of the backsheet 12 chiefly including the areas D adjacent to the waist opening portion and the body-surrounding portion E) of that portion which contacts the diaper wearer's body-surrounding area and waist, through the first and second expansible side panels 20 and 20'.

The first and second expansible side panels 20 and 20' can comprise a woven fabric, non-woven fabric or expansible material made of a block copolymer of styrene and isoprene or butadiene, a copolymer of ethylene, natural rubber, polyurethanes, and a mixture/co-extrudate thereof, or comprise a film of an expansible material, or a composite material of expansible materials. Also, there can be employed a laminated material which is stretch-bonded such that it has universal elasticity, air-permeability, vapor permeability and liquid impermeability. Thus, the materials forming the side panels may be different from the previously discussed materials forming the topsheet.

The laminated material can preferably comprise a melt blown fabric or film of an expansible material such as a block or a graft copolymer of, for example, butadiene, isoprene, styrene, ethylene-ethyl acrylate or a mixture thereof. It can also be a non-woven fabric of a spun bonded polyurethane. Preferably, it can be prepared by the following manner; an elastic or expansible layer is expanded or stretched to some extent, a non-stretched layer is placed on the stretched elastic layer, these layers are bonded together to form a laminate, and the laminate is relaxed so that the elastic layer makes a gathering of the remaining layer.

The first and second expansible side panels 20 and 20' may comprise a laminated material comprising an air-permeable, expansible film held in a non-stretched state, and textile webs, which have been subjected to carding in a machine direction. The film is sandwiched between the textile webs by adhesive means such as heat sealing, ultrasonic sealing, an adhesive or the like in such a manner that the adhesive means are applied linearly in parallel with the machine direction of the textile webs. With this type, a baby or its mother spreads the diaper in the lateral direction so that area in the textile webs, which are not linearly affixed, are ruptured and relaxed to provide a gathering.

The body-surrounding portion elastic materials 21 and 21' and the waist portion elastic materials 23 and 23' can comprise the same material which forms the leg portion elastic members 22 and 22'.

In the disposable diaper of the present invention, it is preferred that the waist portion elastic members in the area adjacent to the waist opening portion are different in contracting stress from the body-surrounding portion elastic members in the body-surrounding areas, and said elastic members in the areas adjacent to said waist opening portion have a greater stress at a 50% stretch than said elastic members in said body-surrounding portion.

Furthermore, in the disposable diaper of the present invention, the elastic members in the back-side portion and the stomach-side portion defining the waist opening portion are preferably different in stress at a 50% stretch.

More specifically, the contracting stress of the elastic members in the areas adjacent to the waist opening portion are preferably in the range from about 30 g/25 mm width to about 300 g/25 mm width at 120% to 200% stretch, and more preferably in the range from about 100 g/25 mm width to about 200 g/25 mm width. The contracting stress of the elastic members of the body-surrounding portion is preferably smaller than the contracting stress of the elastic members of the waist opening portion.

The disposable diaper of this embodiment can easily be manufactured by arranging the various component parts on predetermined locations by means of a known method.

Further embodiments of a pull-on type disposable diaper of the present invention will now be described with reference to FIGS. 3, 4, 5 and 6. Those parts, which are not particularly mentioned, are the same as in the above-mentioned embodiment.

Figure 3:
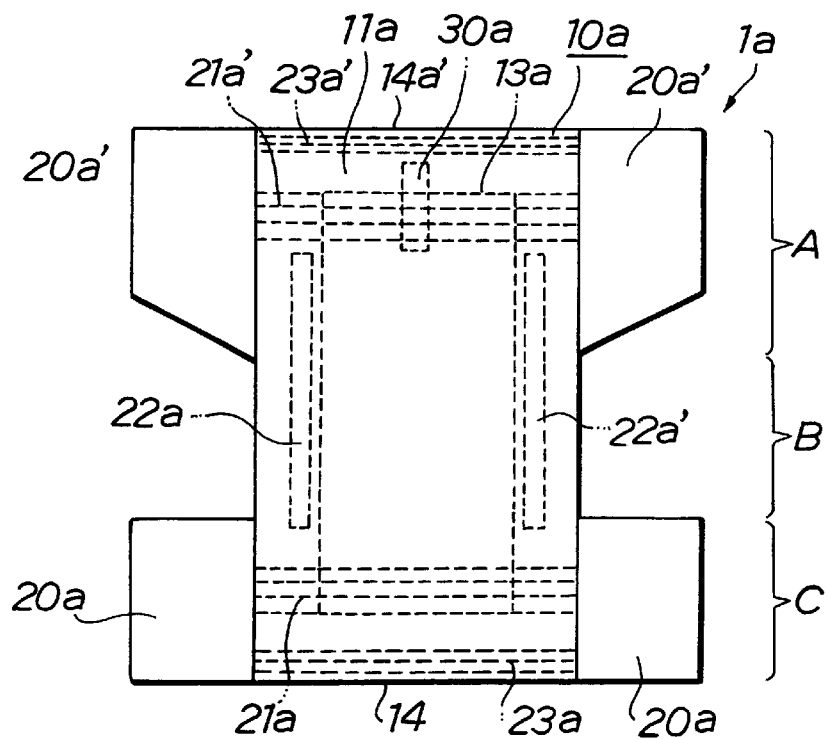
FIG. 3 is another embodiment of a pull-on type disposable diaper of the present invention (which corresponds to FIG. 2)
Figure 4:
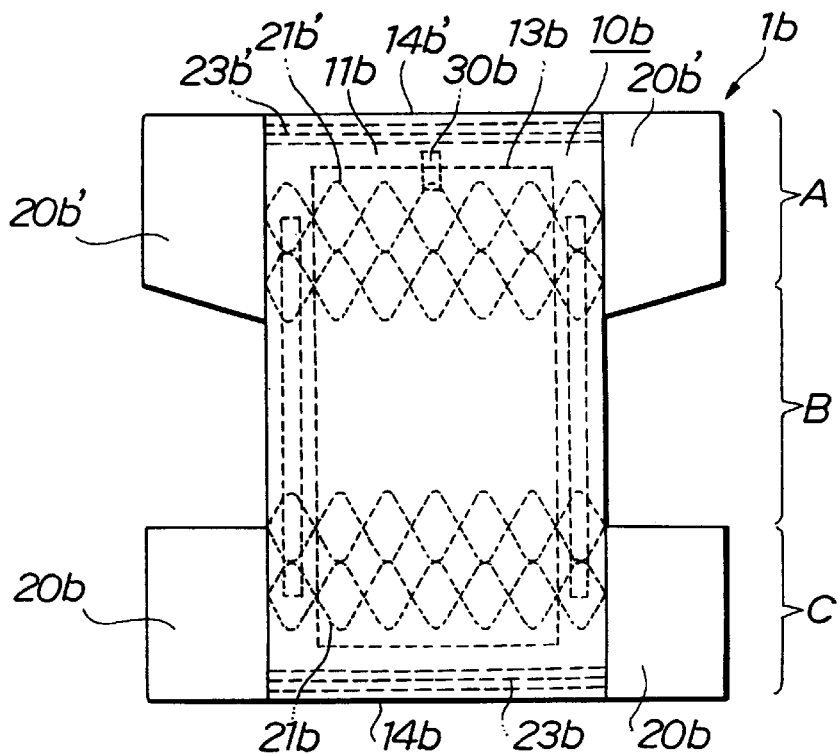
FIG. 4 is a further embodiment of a pull-on type disposable diaper of the present invention (which corresponds to FIG. 2)
Figure 5:
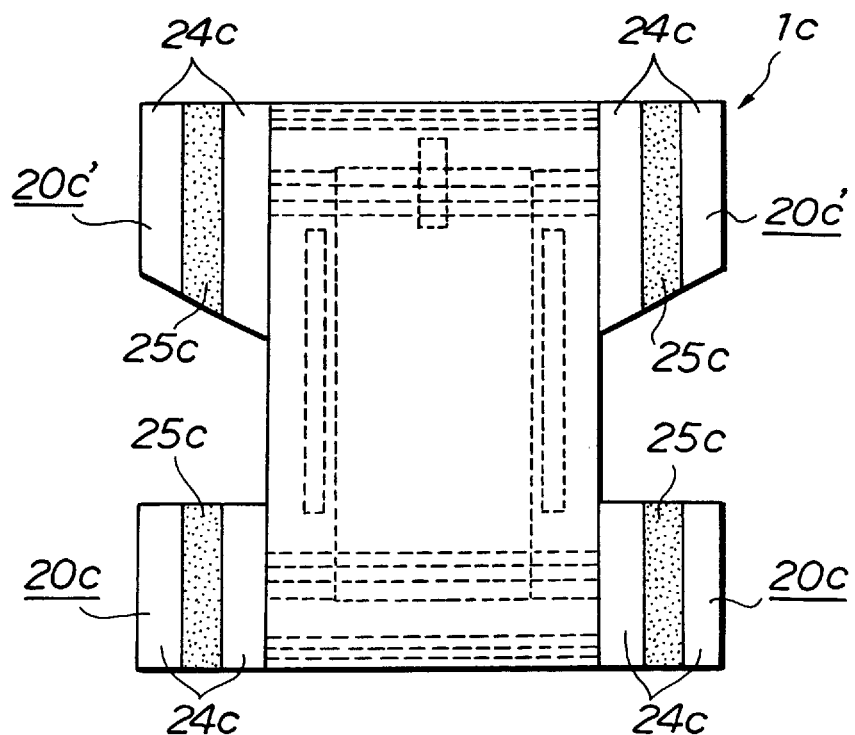
FIG. 5 is still a further embodiment of a pull-on type disposable diaper of the present invention (which corresponds to FIG. 2)
Figure 6:
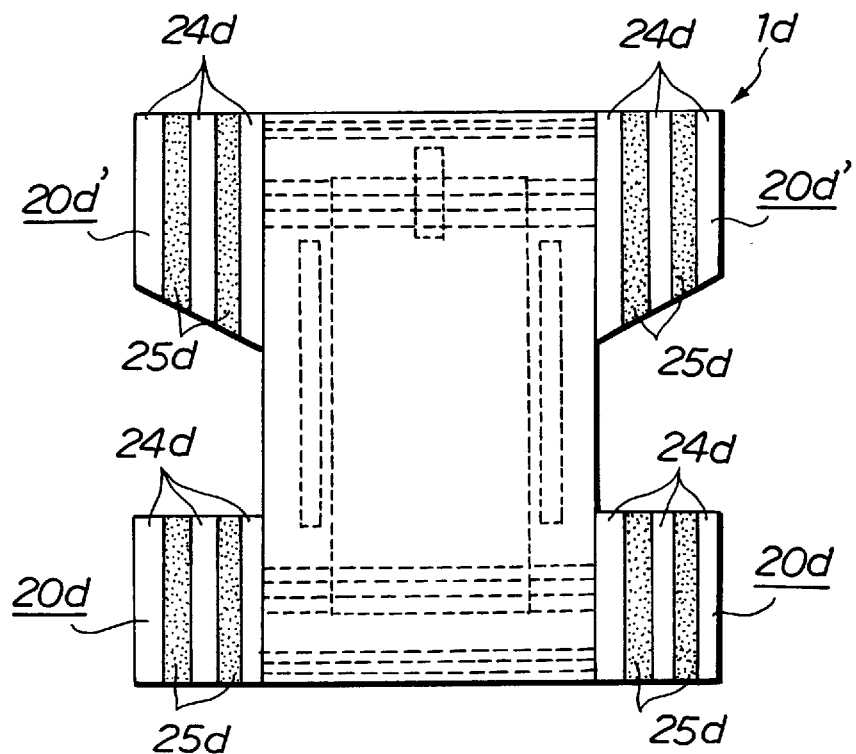
FIG. 6 is yet a further embodiment of a pull-on type disposable diaper of the present invention (which corresponds to FIG. 2).

FIG. 3 is a modified view (which corresponds to FIG. 2) showing another embodiment of a pull-on type disposable diaper of the present invention. FIGS. 4, 5 and 6 are modifications (all of which correspond to FIG. 2) showing still other embodiments of a pull-on type disposable diaper of the present invention.

In a disposable diaper 1a shown in FIG. 3, waist portion elastic members 23a and 23a' in the areas D adjacent to the waist opening portion are of a string-like configuration. Three elastic members 23a and three elastic members 23a' are arranged substantially in parallel with a peripheral edge of the waist opening portion, i.e., the front and back waist portions 14a and 14a', with a predetermined space.

In the case where the waist portion elastic members 23a and 23a' and the body-surrounding portion elastic members 21a and 21a' are comprised of a plurality of elastic materials as mentioned above, the number of the material is not particularly limited.

In a disposable diaper 1b shown in FIG. 4, waist portion elastic members 23b and 23b' in the areas D adjacent to the waist opening portion are of a string-like configuration. Three elastic members 23b and three elastic members 23b' are arranged substantially in parallel with a peripheral edge of the waist opening portion, i.e., the front and back waist portions 14b and 14b', with a predetermined space. Also, the body-surrounding portion elastic members 21b and 21b' of the body-surrounding portions E are arranged in such a manner that at least a part of the elastic members 21b and 21b' cooperatively form loops.

In this way, in the disposable diaper 1b of this embodiment, a fit property of the diaper at the body-surrounding portions is enhanced, since the elastic members 21b and 21b' of the body-surrounding portions E are arranged in such a manner that at least a part of them cooperatively form loops.

In disposable diapers 1c and 1d respectively shown in FIGS. 5 and 6, expansible side panels 20c, 20c' and 20d, 20d' are respectively comprised of non-expansible portions 24c and 24d which are formed of a non-expansible material, and expansible portions 25c and 25d which are formed of an expansible material. Owing to the employment of this arrangement, the stress concentration on the area around each leg portion of the diaper wearer can be dispersed.

In the above-mentioned embodiment, the shape of each loop is rectangular as one example. However, the shape of the loop is not limited to this, and it may be circular, elliptical or the like. Also, each expansible side panel may be formed by fixedly sandwiching an expansible member of a thermoplastic polyurethane, an olefinic foamed elastomer or the like with non-expansible members respectively placed on the top and bottom of the expansible member and then forming slits in each of the non-expansible members, the slit being in parallel with the longitudinal direction of the diaper, so that the expansible side panel can be expanded and contracted in a lateral direction.

It should be understood that the present invention is not limited to the above-mentioned embodiments and various modifications can be made without departing from the scope of the invention.

What is claimed is:

1. A pull-on disposable diaper comprising:

a rectangular body having opposing longitudinal sides, said body further having a topsheet formed of a liquid permeable first material, a backsheet formed of a liquid impermeable second material different from said first material, and an absorbent member interposed between said topsheet and said backsheet;

a stomach-side portion located on a stomach side of a diaper wearer when the diaper is worn, a back-side portion located on a back side of the wearer when the diaper is worn, and a crotch portion located between said stomach-side portion and said back-side portion;

a pair of first expansible side panels separately formed of a third material different from said first material, each of said first expansible side panels being affixed to said opposing longitudinal sides of said body adjacent to said stomach-side portion;

a pair of second expansible side panels separately formed of said third material, each of said second expansible side panels being affixed to said opposing longitudinal sides of said body adjacent to said back-side portion;

affixing means for affixing said pair of first expansible side panels to said opposing longitudinal sides of said body adjacent to said stomach-side portion and for affixing said pair of second expansible side panels to said opposing longitudinal sides of said body adjacent to said back-side portion;

said first expansible side panels of said stomach-side portion being affixed to said second expansible side panels of said back-side portion to thereby define a waist opening portion, a pair of leg opening portions and a body-surrounding portion located around the wearer's body when the diaper is worn; and first elastic members arranged on an area adjacent to said waist opening portion and second elastic members arranged on said body-surrounding portion in said stomach-side and back-side portions, each of said first and second elastic members having opposing ends which terminate within said body;

wherein a substantially continuous gather is formed along an entire periphery of the diaper through said stomach-side portion, said back-side portion and said first and second expansible side panels, and wherein a plurality of said first elastic members in the area adjacent to said waist opening portion are arranged substantially in parallel with a peripheral edge of said waist opening portion with a predetermined space between each of said plurality of first elastic members; and said second elastic members in said body-surrounding portion are arranged in such a manner that at least a part of said second elastic members cooperatively form a loop.

2. The pull-on disposable diaper as claimed in claim 1, wherein said first elastic members in said back-side portion and said stomach-side portion defining said waist opening portion are different in stress at 50% stretch.

3. A pull-on disposable diaper comprising:

a rectangular body having opposing longitudinal sides, said body further having a topsheet formed of a liquid permeable first material, a backsheet formed of a liquid impermeable second material different from said first material, and an absorbent member interposed between said topsheet and said backsheet;

a stomach-side portion located on a stomach side of a diaper wearer when the diaper is worn, a back-side portion located on a back side of the wearer when the diaper is worn, and a crotch portion located between said stomach-side portion and said back-side portion;

a pair of first expansible side panels separately formed of a third material different from said first material, each of said first expansible side panels being affixed to said opposing longitudinal sides of said body adjacent to said stomach-side portion;

a pair of second expansible side panels separately formed of said third material, each of said second expansible side panels being affixed to said opposing longitudinal sides of said body adjacent to said back-side portion;

affixing means for affixing said pair of first expansible side panels to said opposing longitudinal sides of said body adjacent to said stomach-side portion and for affixing said pair of second expansible side panels to said opposing longitudinal sides of said body adjacent to said back-side portion;

said first expansible side panels of said stomach-side portion being affixed to said second expansible side panels of said back-side portion to thereby define a waist opening portion, a pair of leg opening portions and a body-surrounding portion located around the wearer's body when the diaper is worn; and first elastic members arranged on an area adjacent to said waist opening portion and second elastic members arranged on said body-surrounding portion in said stomach-side and back-side portions, each of said first and second elastic members having opposing ends which terminate within said body;

wherein a substantially continuous gather is formed along an entire periphery of the diaper through said stomach-side portion, said back-side portion and said first and second expansible side panels, and wherein said first elastic members in the areas adjacent to said waist opening portion are different in contracting stress from said second elastic members in said body-surrounding portions and said first elastic members in the areas adjacent to said waist opening portion have a greater stress at 50% stretch than said second elastic members in said body-surrounding portion.

4. The pull-on disposable diaper as claimed in claim 2, wherein said first elastic members in said back-side portion and said stomach-side portion defining said waist opening portion are different in stress at 50% stretch.

5. A pull-on disposable diaper comprising:

a rectangular body having opposing longitudinal sides, said body further having a topsheet formed of a liquid permeable first material, a backsheet formed of a liquid impermeable second material different from said first material, and an absorbent member interposed between said topsheet and said backsheet;

a stomach-side portion located on a stomach side of a diaper wearer when the diaper is worn, a back-side portion located on a back side of the wearer when the diaper is worn, and a crotch portion located between said stomach-side portion and said back-side portion;

a pair of first expansible side panels separately formed of a third material different from said first material, each of said first expansible side panels being affixed to said opposing longitudinal sides of said body adjacent to said stomach-side portion;

a pair of second expansible side panels separately formed of said third material, each of said second expansible side panels being affixed to said opposing longitudinal sides of said body adjacent to said back-side portion;

affixing means for affixing said pair of first expansible side panels to said opposing longitudinal sides of said body adjacent to said stomach-side portion and for affixing said pair of second expansible side panels to said opposing longitudinal sides of said body adjacent to said back-side portion;

said first expansible side panels of said stomach-side portion being affixed to said second expansible side panels of said back-side portion to thereby define a waist opening portion, a pair of leg opening portions and a body-surrounding portion located around the wearer's body when the diaper is worn; and first elastic members arranged on an area adjacent to said waist opening portion and second elastic members arranged on said body-surrounding portion in said stomach-side and back-side portions, each of said first and second elastic members having opposing ends which terminate within said body;

wherein a substantially continuous gather is formed along an entire periphery of the diaper through said stomach-side portion, said back-side portion and said first and second expansible side panels, and wherein said first elastic members in said back-side portion and said stomach-side portion defining said waist opening portion are different in stress at 50% stretch.

6. A pull-on disposable diaper comprising:

a rectangular body having opposing longitudinal sides, said body further having a topsheet formed of a liquid permeable first material, a backsheet formed of a liquid impermeable second material different from said first material, and an absorbent member interposed between said topsheet and said backsheet;

a stomach-side portion located on a stomach side of a diaper wearer when the diaper is worn, a back-side portion located on a back side of the wearer when the diaper is worn, and a crotch portion located between said stomach-side portion and said back-side portion;

a pair of first expansible side panels separately formed of a third material different from said first material, each of said first expansible side panels being affixed to said opposing longitudinal sides of said body adjacent to said stomach-side portion;

a pair of second expansible side panels separately formed of said third material, each of said second expansible side panels being affixed to said opposing longitudinal sides of said body adjacent to said back-side portion;

affixing means for affixing said pair of first expansible side panels to said opposing longitudinal sides of said body adjacent to said stomach-side portion and for affixing said pair of second expansible side panels to said opposing longitudinal sides of said body adjacent to said back-side portion;

said first expansible side panels of said stomach-side portion being affixed to said second expansible side panels of said back-side portion to thereby define a waist opening portion, a pair of leg opening portions and a body-surrounding portion located around the wearer's body when the diaper is worn; and first elastic members arranged on an area adjacent to said waist opening portion and second elastic members arranged on said body-surrounding portion in said stomach-side and back-side portions, each of said first and second elastic members having opposing ends which terminate within said body;

wherein a substantially continuous gather is formed along an entire periphery of the diaper through said stomach-side portion, said back-side portion and said first and second expansible side panels, and wherein said first and second expansible side panels are formed of longitudinally arranged alternating expansible and non-expansible portions.

7. The pull-on disposable diaper as claimed in claim 6, wherein there is provided a single expansible portion between two non-expansible portions for each expansible panel.

8. The pull-on disposable diaper as claimed in claim 6, wherein there is provided at least two expansible portions alternating with at least two non-expansible portions for each expansible panel.

* * * * *